US009504579B2

(12) United States Patent
Mahfouz et al.

(10) Patent No.: US 9,504,579 B2
(45) Date of Patent: *Nov. 29, 2016

(54) METHODS OF PREDETERMINING THE CONTOUR OF A RESECTED BONE SURFACE AND ASSESSING THE FIT OF A PROSTHESIS ON THE BONE

(75) Inventors: Mohamed Mahfouz, Knoxville, TN (US); Brian D. Earl, South Bend, IN (US)

(73) Assignees: Zimmer, Inc., Warsaw, IN (US); Mohamed Mahfouz, Knoxville, TN (US)

( * ) Notice: Subject to any disclaimer, the term of this patent is extended or adjusted under 35 U.S.C. 154(b) by 925 days.

This patent is subject to a terminal disclaimer.

(21) Appl. No.: 13/533,552

(22) Filed: Jun. 26, 2012

(65) Prior Publication Data

US 2012/0265499 A1    Oct. 18, 2012

Related U.S. Application Data

(62) Division of application No. 11/685,906, filed on Mar. 14, 2007, now Pat. No. 8,231,634.

(60) Provisional application No. 60/783,630, filed on Mar. 17, 2006.

(51) Int. Cl.
*A61B 34/10* (2016.01)
*A61F 2/30* (2006.01)
(Continued)

(52) U.S. Cl.
CPC .......... *A61F 2/30942* (2013.01); *A61B 5/1075* (2013.01); *A61B 5/1077* (2013.01); *A61B 5/4528* (2013.01); *A61B 34/10* (2016.02); *A61F 2/3859* (2013.01); *A61F 2002/30892* (2013.01); *A61F 2002/30948* (2013.01)

(58) Field of Classification Search
CPC ................. A61F 2/30942; A61F 2002/30943; A61F 2002/30945; A61F 2002/30948; A61F 2002/3095; A61F 19/50; A61F 2019/502
USPC ............................................... 606/86 R, 102
See application file for complete search history.

(56) References Cited

U.S. PATENT DOCUMENTS 4,549,540 A    10/1985  Caspari et al.
4,913,413 A     4/1990  Raab et al.
(Continued)

FOREIGN PATENT DOCUMENTS

AU    2007227129       9/2012
DE    2821247A1 A1   11/1979
(Continued)

OTHER PUBLICATIONS

"Closed-form solution of absolute orientation using unit quaternions" Berthold K. P. Horn, Reprinted from Journal of the Optical Society of America A. vol. 4, p. 629, Apr. 1987 Optical Society of America, pp. 629-642.
(Continued)

*Primary Examiner* — Anu Ramana
(74) *Attorney, Agent, or Firm* — Schwegman Lundberg & Woessner, P.A.

(57) ABSTRACT

Methods for predetermining a contour of a resected bone surface and assessing a fit of a prosthesis on the resected bone surface, for designing prostheses to fit discrete patient populations, and for designing customized prostheses.

11 Claims, 4 Drawing Sheets

(51) Int. Cl.
  *A61B 5/107* (2006.01)
  *A61B 5/00* (2006.01)
  *A61F 2/38* (2006.01)

(56) References Cited

U.S. PATENT DOCUMENTS

| | | | |
|---|---|---|---|
| 4,936,862 | A | 6/1990 | Walker et al. |
| 5,030,237 | A | 7/1991 | Sorbie et al. |
| 5,403,319 | A | 4/1995 | Matsen, III et al. |
| 5,408,409 | A | 4/1995 | Glassman et al. |
| 5,540,696 | A | 7/1996 | Booth, Jr. et al. |
| 5,682,886 | A | 11/1997 | Delp et al. |
| 5,792,147 | A | 8/1998 | Evans et al. |
| 5,828,813 | A | 10/1998 | Ohm |
| 5,834,759 | A | 11/1998 | Glossop |
| 5,871,018 | A | 2/1999 | Delp et al. |
| 5,921,992 | A | 7/1999 | Costales et al. |
| 6,006,126 | A | 12/1999 | Cosman |
| 6,096,050 | A | 8/2000 | Audette |
| 6,160,264 | A | 12/2000 | Rebiere |
| 6,197,017 | B1 | 3/2001 | Brock et al. |
| 6,205,411 | B1 | 3/2001 | DiGioia, III et al. |
| 6,233,504 | B1 | 5/2001 | Das et al. |
| 6,338,716 | B1 | 1/2002 | Hossack |
| 6,348,058 | B1 | 2/2002 | Melkent et al. |
| 6,430,434 | B1 | 8/2002 | Mittelstadt |
| 6,434,507 | B1 | 8/2002 | Clayton et al. |
| 6,450,978 | B1 | 9/2002 | Brosseau et al. |
| 6,470,207 | B1 | 10/2002 | Simon et al. |
| 6,490,467 | B1 | 12/2002 | Bucholz et al. |
| 6,490,475 | B1 | 12/2002 | Seeley |
| 6,491,699 | B1 | 12/2002 | Henderson et al. |
| 6,510,334 | B1 | 1/2003 | Schuster et al. |
| 6,533,737 | B1 | 3/2003 | Brosseau et al. |
| 6,697,664 | B2 | 2/2004 | Kienzle III et al. |
| 6,701,174 | B1 | 3/2004 | Krause et al. |
| 6,772,026 | B2 | 8/2004 | Bradbury et al. |
| 6,932,842 | B1 | 8/2005 | Litschko et al. |
| 7,024,032 | B2 | 4/2006 | Kidd et al. |
| 7,029,477 | B2 | 4/2006 | Grimm |
| 7,039,225 | B2 | 5/2006 | Tanaka et al. |
| 7,194,295 | B2 | 3/2007 | Vilsmeier |
| 7,234,937 | B2 | 6/2007 | Sachdeva et al. |
| 7,242,999 | B2 | 7/2007 | Wang |
| 7,275,023 | B2 | 9/2007 | Chen et al. |
| 7,587,075 | B1 | 9/2009 | Stefan et al. |
| 7,634,306 | B2 | 12/2009 | Sarin et al. |
| 7,646,901 | B2 | 1/2010 | Murphy et al. |
| 8,231,634 | B2 | 7/2012 | Mahfouz et al. |
| 2002/0068942 | A1 | 6/2002 | Neubauer et al. |
| 2003/0033127 | A1 | 2/2003 | Lett |
| 2003/0130665 | A1 | 7/2003 | Pinczewski et al. |
| 2003/0225415 | A1 | 12/2003 | Richard |
| 2004/0102866 | A1* | 5/2004 | Harris et al. ........... 700/117 |
| 2004/0111183 | A1 | 6/2004 | Sutherland et al. |
| 2004/0122305 | A1 | 6/2004 | Grimm et al. |
| 2004/0146830 | A1 | 7/2004 | Weinstein |
| 2004/0152955 | A1 | 8/2004 | McGinley et al. |
| 2004/0153062 | A1 | 8/2004 | McGinley et al. |
| 2004/0204760 | A1 | 10/2004 | Fitz et al. |
| 2004/0230199 | A1 | 11/2004 | Jansen et al. |
| 2004/0236424 | A1 | 11/2004 | Berez et al. |
| 2005/0076521 | A1 | 4/2005 | Said |
| 2005/0119564 | A1 | 6/2005 | Rosholm et al. |
| 2005/0197814 | A1 | 9/2005 | Aram et al. |
| 2005/0198849 | A1 | 9/2005 | Goeggelmann et al. |
| 2005/0234332 | A1 | 10/2005 | Murphy |
| 2006/0094951 | A1 | 5/2006 | Dean et al. |
| 2006/0100498 | A1 | 5/2006 | Boyce et al. |
| 2006/0100832 | A1 | 5/2006 | Bowman |
| 2006/0161051 | A1 | 7/2006 | Terrill-Grisoni et al. |
| 2006/0204067 | A1 | 9/2006 | Tuma et al. |
| 2006/0216681 | A1 | 9/2006 | Walker et al. |
| 2006/0229624 | A1 | 10/2006 | May et al. |
| 2007/0066893 | A1 | 3/2007 | Eriksen et al. |
| 2007/0066917 | A1 | 3/2007 | Hodorek et al. |
| 2007/0123894 | A1 | 5/2007 | Claypool et al. |
| 2007/0156066 | A1 | 7/2007 | McGinley |
| 2007/0156157 | A1 | 7/2007 | Nahum et al. |
| 2007/0203605 | A1 | 8/2007 | Melton et al. |
| 2007/0255288 | A1 | 11/2007 | Mahfouz et al. |
| 2007/0274442 | A1 | 11/2007 | Gregory et al. |
| 2008/0163344 | A1 | 7/2008 | Yang |
| 2008/0167547 | A1 | 7/2008 | Bova et al. |
| 2009/0048597 | A1 | 2/2009 | Heavener |
| 2009/0089034 | A1 | 4/2009 | Penney et al. |

FOREIGN PATENT DOCUMENTS

| | | |
|---|---|---|
| EP | 1406203A2 A2 | 4/2004 |
| EP | 2001411 B1 | 5/2013 |
| FR | 2776176A2 A2 | 3/1998 |
| WO | WO94/23605 A1 | 10/1994 |
| WO | WO99/37220 A1 | 7/1999 |
| WO | WO00/03210 A1 | 1/2000 |
| WO | WO03/030738 A1 | 4/2003 |
| WO | WO2004/017842 A2 | 3/2004 |
| WO | WO2004/019792 A1 | 3/2004 |

OTHER PUBLICATIONS

"Point Cloud to CAD Model Registration Methods in Manufacturing Inspection" Tucker et al., Journal of Computing and Information Science in Engineering Technology Review, vol. 6, Dec. 2006.

The ISR and WO mailed in related IA No. PCT/US2007/063949 on Jul. 27, 2007.

Taylor et al. Robotic Hip Replacement Surgery in Dogs, Medical Applications of Robotics, IEEE Engineering in Medicine & Biology Society 11th Annual International Conference, 1989.

Article Biomedizinische Technik Band 48, Heft Dec. 2003 "Usability of an Image Based Navigation System in Reconstruction of Leg Alignment in Total Knee Arthroplasty—Results of a Prospective Study," Perlick et al, pp. 339-343.

Article The Journal of Arthroplasty vol. 16, No. 5 (2001) "The Effect of Surgeon Experience on Component Positioning in 673 Press Fit Condylar Posterior Cruciate—Sacrificing Totla Knee Arthroplasties," Mahaluxmivala et al., pp. 635-340.

Article Acta Orthop Scand 2004: 75, "Navigation in Total Knee Arthroplasty CT-Based Implantation Compared With the Conventional Technique," Perlick et al., pp. 464-470.

Kienzle et al "Total Knee Replacement" IEEE Engineering in Medicine and Biology Magazine, IEEE Inc. New York, vol. 14, No. 3, May 1, 1995, p. 301-306.

Viceconti, Marco, et al., An automated method to position prosthetic components within multiple anatomical spaces, Computer Methods and Programs in Biomedicine, 2003, 121-127, V.70 No. 2, Istituti Ortopedici Rizzoli, Bologna, Italy.

Testi, Debora, et al., JIDE: a new software for computer-aided design of hip prosthesis, Computer Methods and Programs in Biomedicine, 2004, 213-220, V.75 No. 3, Istituti Ortopedici Rizzoli, Bologna, Italy Testi.

Viceconti, Marco, et al., TRI2SOLIDE: an application of reverse engineering methods to the creation of CAD models of bone segments, Computer Methods and Programs in Biomedicine, 1998, 211-220, V.56 No. 3, Istituti Ortopedici Rizzoli, Bologna, Italy.

Office Action mailed Jul. 2, 2010 from the European Patent Office in related European Patent Application No. 07758498.5.

International Preliminary Report on Patentability issued Sep. 23, 2008 in related International Patent Application No. PCT/US2007/063949.

"U.S. Appl. No. 11/685,906, Final Office Action mailed Dec. 16, 2011", 6 pgs.

"U.S. Appl. No. 11/685,906, Non Final Office Action mailed Jun. 17, 2011".

"U.S. Appl. No. 11/685,906, Notice of Allowance mailed Apr. 3, 2012", 8 pgs.

"U.S. Appl. No. 11/685,906, Response filed Mar. 1, 2012 to Final Office Action mailed Dec. 16, 2011", 8 pgs.

(56) References Cited

OTHER PUBLICATIONS

"U.S. Appl. No. 11/685,906, Response filed Apr. 15, 2011 to Restriction Requirement mailed Mar. 30, 2011", 7 pgs.
"U.S. Appl. No. 11/685,906, Response filed Aug. 26, 2010 to Non Final Office Action mailed Jun. 17, 2010", 10 pgs.
"U.S. Appl. No. 11/685,906, Restriction Requirement mailed Mar. 30, 2011", 6 pgs.
"Australian Application Serial No. 2007227129, Examination Report mailed Feb. 2, 2012", 3 pgs.
"Australian Application Serial No. 2007227129, Response filed May 21, 2012 to Examination Report dated Feb. 2, 2012", 23 pgs.
"European Application Serial No. 07758498.5, Office Action mailed Mar. 26, 2012", 1 pg.
"European Application Serial No. 07758498.5, Office Action mailed Oct. 31, 2008", 2 pgs.
"European Application Serial No. 07758498.5, Response filed Oct. 28, 2010 to Office Action mailed Jul. 2, 2010", 8 pgs.
"Japanese Application Serial No. 2009-50059, Office Action mailed Oct. 2, 2012", w/English Translation, 4 pgs.
"Japanese Application Serial No. 2009-50059, Response filed Dec. 27, 2012 to Office Action mailed Oct. 2, 2012", w/English Claims, 12 pgs.
"Japanese Application Serial No. 2009-500591, Office Action mailed Feb. 9, 2012", English Translation, 13 pgs.
"Japanese Application Serial No. 2009-500591, Response filed Apr. 5, 2012 to Office Action mailed Feb. 9, 2012", w/English Claims, 15 pgs.
"Biomet Orthopedics, Inc., Product Detail Signature Personalized Patient Care", (2008), 1 pg.
"Biomet Orthopedics, Inc., Signature Personalized Arthritis Care", (2008, 2009), 2 pgs.
"Minimally Invasive Surgical Technique (MIS), Intramedullary Surgical Approach", MIS, the MIG Unicompartmental Knee, Zimmer, (2002), 26 pgs.
"Surgical Technique—Nexgen Complete Knee Solution for the Legacy Knee LPS-Flex Fixed Bearing Knee", Zimmer, Inc., (2004, 2007), 12 pgs.

* cited by examiner

METHODS OF PREDETERMINING THE CONTOUR OF A RESECTED BONE SURFACE AND ASSESSING THE FIT OF A PROSTHESIS ON THE BONE

CROSS REFERENCE TO RELATED APPLICATIONS

The present application is a divisional application of U.S. patent application Ser. No. 11/685,906, titled METHODS OF PREDETERMINING THE CONTOUR OF A RESECTED BONE SURFACE AND ASSESSING THE FIT OF A PROSTHESIS ON THE BONE, which claims the benefit under Title 35, U.S.C. §119(e) of U.S. Provisional Patent Application Ser. No. 60/783,630, entitled METHODS OF PREDETERMINING THE CONTOUR OF A RESECTED BONE AND THE FIT OF AN IMPLANT ON THE BONE, filed Mar. 17, 2006, the disclosures of which are hereby expressly incorporated herein by reference.

BACKGROUND

The present disclosure relates to methods for determining an optimal fit of a prosthesis on a resected bone surface, Orthopaedic procedures for the replacement of all, or a portion of, a patient's joint typically require resecting and reshaping of the bones of the joint to receive prosthetic components. For example, a typical total knee prosthesis has three main components: a femoral component for replacing at least a portion of the distal end of the femur, a tibial component for replacing at least a portion of the proximal end of the tibia, and a bearing insert for replacing at least a portion of the articulating tissue between the femur and the tibia. Procedures for implanting a total knee prosthesis typically involve preparing and reshaping both the distal end of the femur and the proximal end of the tibia prior to implanting the prosthetic components. The amount of bone removed may be partially determined by the size and type of prosthetic components to be implanted, The size of prosthetic components may be initially determined by measurements taken of the knee prior to and during surgery, and the final determination of size may be made after taking measurements and trialing a provisional prosthesis during the procedure.

SUMMARY

The present disclosure provides methods for predetermining a contour of a resected bone surface and assessing a fit of a prosthesis on the resected bone surface. The present disclosure also provides methods for designing prostheses to fit discrete patient populations as well as methods for designing customized prostheses.

In one form thereof, the present disclosure provides a method of virtually assessing the fit of a prosthesis for placement on a resected bone surface, the method including the steps of creating a two-dimensional outline of the resected bone surface; creating a two-dimensional outline of a first prosthesis; and comparing the two-dimensional outline of the resected bone surface with the two-dimensional outline of the first prosthesis.

In another form thereof, the present disclosure provides an apparatus for virtually assessing the fit of a prosthesis for placement on a resected bone surface, the apparatus including a first computer adapted to create a two-dimensional outline of the resected bone surface; second computer for creating a two-dimensional outline of a first prosthesis; and a third computer for comparing the two-dimensional outline of the resected bone surface with the two-dimensional outline of the first prosthesis.

In yet another form thereof, the present disclosure provides a method of designing a prosthesis to substantially fit a resected bone surface based on a population of bones, the method including the steps of creating a plurality of two-dimensional outlines corresponding to each resected bone surface for each bone of the population; and determining a contour of a bone engaging surface of a prosthesis using the plurality of two-dimensional outlines, wherein the contour substantially matches the plurality of two-dimensional outlines of the resected bone surfaces.

In still another form thereof, the present disclosure provides an apparatus for designing a prosthesis to substantially fit a resected bone surface based on a population of bones, the apparatus including a first computer for creating a plurality of two-dimensional outlines corresponding to each resected bone surface for each bone of the population; and a second computer for determining a contour of a bone engaging surface of a prosthesis which substantially matches the plurality of two-dimensional outlines of the resected bone surfaces.

In one form thereof, the present disclosure provides a method of creating a prosthesis for placement on a resected bone surface, the method including the steps of creating a two-dimensional outline of the resected bone surface; and determining a contour of a bone engaging surface of a prosthesis using the two-dimensional outline of the resected bone surface.

In another form thereof the present disclosure provides an apparatus for creating a prosthesis for placement on a resected bone surface, the apparatus including a first computer for creating a two-dimensional outline of the resected bone surface; and a second computer for determining a contour of a bone engaging surface of a prosthesis using the two-dimensional outline of the resected bone surface.

BRIEF DESCRIPTION OF THE DRAWINGS

The above mentioned and other features of the disclosure, and the manner of attaining them, will become more apparent and will be better understood by reference to the following description of embodiments of the disclosure taken in conjunction with the accompanying drawings, wherein.

Figure 1:
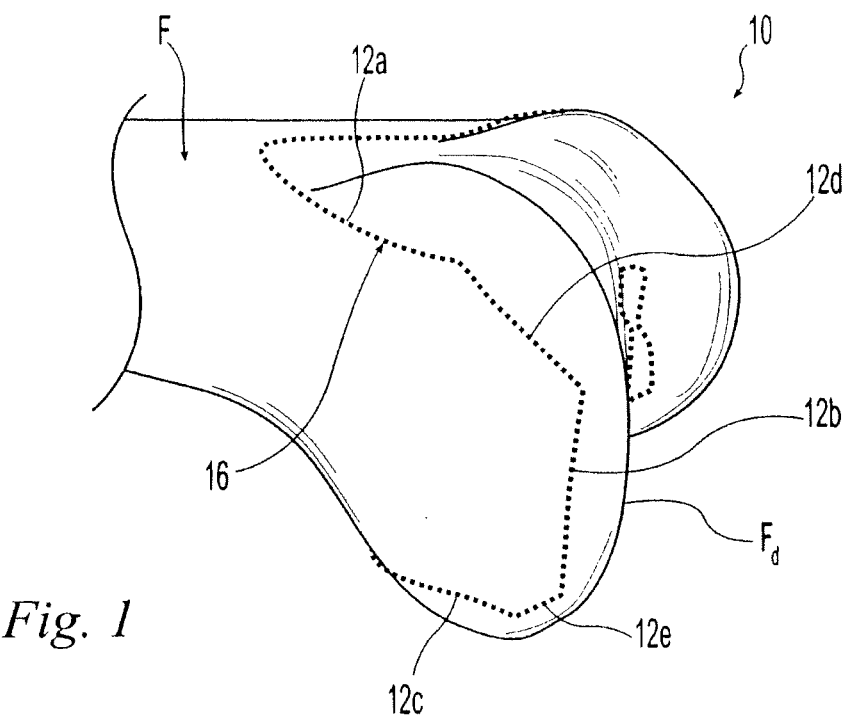
FIG. 1 is a perspective view of a digital model of the distal end of a femur including a virtual resection according to an exemplary method of the present disclosure.

Corresponding reference characters indicate corresponding parts throughout the several views. Although the drawings represent embodiments of the present disclosure, the drawings are not necessarily to scale and certain features may be exaggerated in order to better illustrate and explain the present disclosure. Although the exemplifications set out herein illustrate embodiments of the disclosure, the embodiments disclosed below are not intended to be exhaustive or to be construed as limiting the scope of the invention to the precise forms disclosed.

DETAILED DESCRIPTION

The present disclosure may include references to the following terms: anterior (at or near the front of the body, as opposed to the back of the body); posterior (at or near the back of the body, as opposed to the front of the body); lateral (at or near the side of the body, farther from the midsagittal plane, as opposed to medial); medial (at or near the middle of the body, at or near the midsagittal plane, as opposed to lateral); proximal (toward the beginning, at or near the head of the body, as opposed to distal); and distal (further from the beginning, at or near the foot of the body, as opposed to proximal).

Referring to FIGS. 1-8, an exemplary method of the present disclosure may be used to determine how a femoral prosthesis will fit on the distal end of a femur, i.e., to assess whether a prosthesis is of the right size and shape for the distal end of the femur and whether the prosthesis suitably conforms thereto. The method generally includes the steps of obtaining a three-dimensional (3-D) model of a bone based on an acquired image of the bone, virtually resecting the 3-D model of the bone, i.e., creating or simulating a resection of the bone within a computer or other intelligent processing device, preparing a bone profile of the virtual resection, creating a two-dimensional (2-D) outline or footprint of the resection from the bone profile, preparing a prosthesis profile, creating a 2-D outline or footprint from the prosthesis profile, and comparing the 2-D outlines of the bone profile and the prosthesis profile to assess or determine the fit of the prosthesis with the bone.

More particularly, referring to FIG. 1, 3-D digital model 10 of an exemplary femur F is illustrated. Digital model 10 may be obtained by obtaining a computed tomography ("CT") scan of a femur to produce a 3-D image of the femur and converting the 3-D image to digital model 10. The conversion of the 3-D CT scan image to 3-D digital model 10 may be performed using any suitable modeling software including, for example, Amira®, available from Mercury Computer Systems, Inc., of Chelmsford, Mass. Digital model 10 may include femur F having distal end $F_d$.

Figure 2:
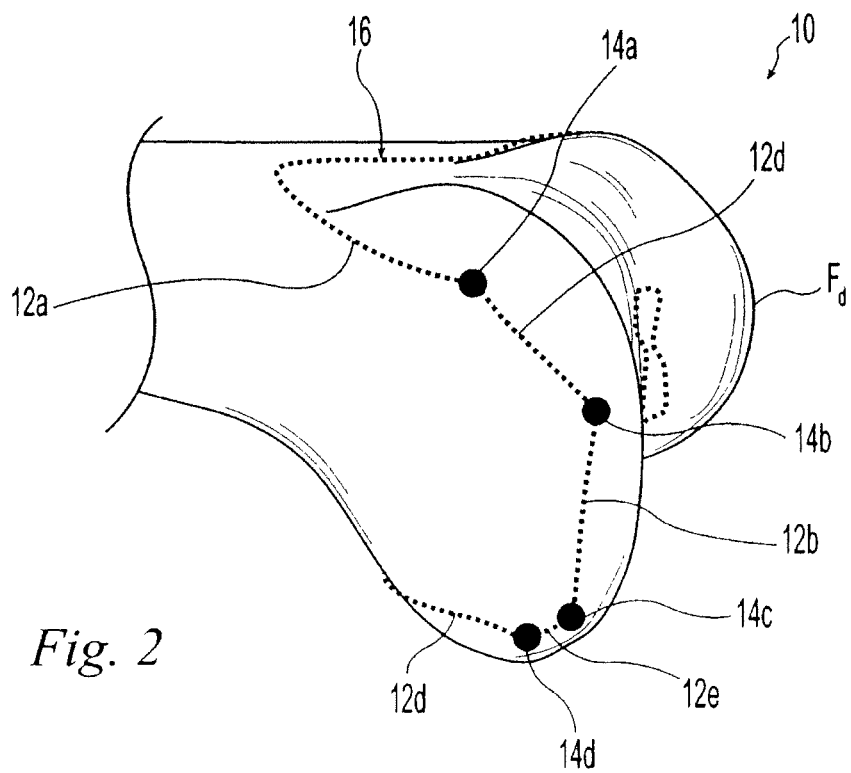
FIG. 2 is a perspective view of the digital model of FIG. 1, further illustrating vertices of the virtual resection.
Figure 3:
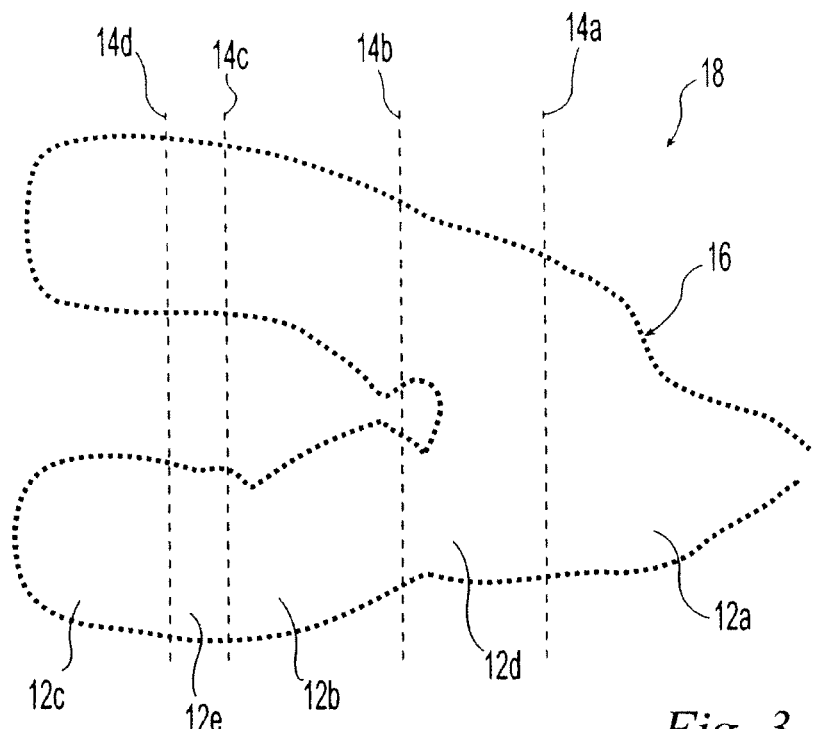
FIG. 3 is atop view of the two-dimensional outline of the femoral resection of FIG. 1.
Figure 4:
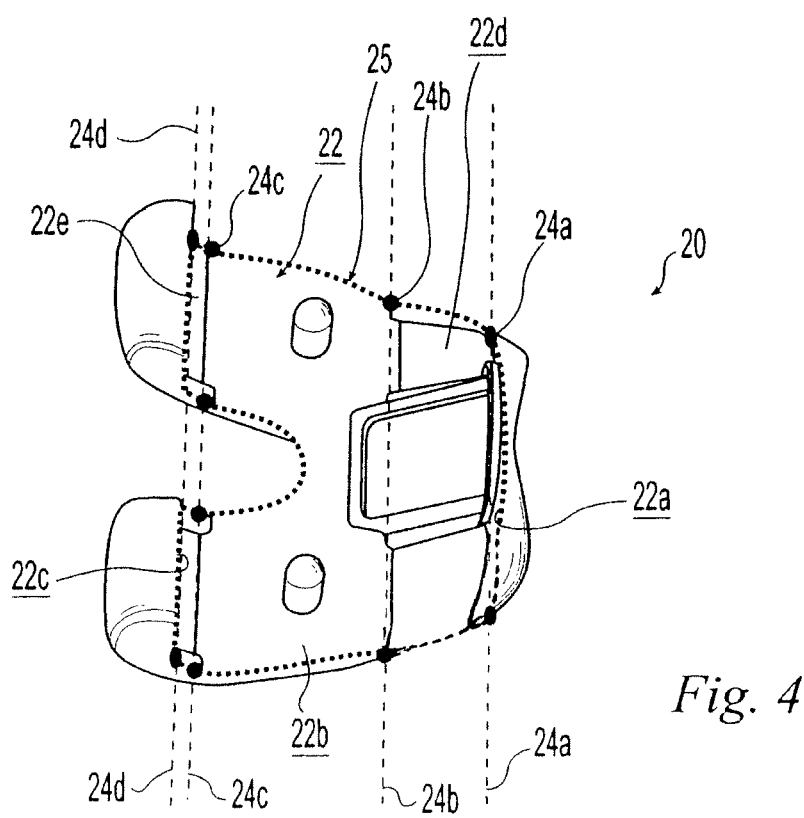
FIG. 4 a perspective view of an exemplary distal femoral prosthesis which may be used in an exemplary method of the present disclosure.

Referring still to FIG. 1, using suitable software, such as MATLAB®, available from The Math Works, of Natick, Mass., and Unigraphics®, available from UGS Corp., of Plano, Tex., a virtual resection of distal end $F_d$ of model femur F is performed. Similar to the resection performed in actual knee arthroplasty procedures, the virtual resection involves defining femoral cut planes 12a-12e on distal end $F_d$; of model femur F. Femoral cut planes 12a-12e are calculated using an algorithm of the software. The algorithm calculates femoral cut planes 12a-12e based on a proposed, exemplary femoral prosthesis and the known surgical technique specified for the proposed femoral prosthesis, More particularly, distal end $F_d$ of model femur F may be preliminarily measured based on the known surgical technique and using the software described above. The resulting measurements are used to preliminarily select a femoral prosthesis size and type. Resection of distal end $F_d$ of model femur F is determined by the selected femoral prosthesis and involves resecting distal end $F_d$ of femur F to complement and receive the prosthesis, For example, as shown in FIG. 4, model femoral prosthesis 20 may be preliminarily selected. Femoral prosthesis 20 is a cruciate-retaining femoral prosthetic component having bone engaging surface 22, Bone engaging surface 22 includes a plurality of intersecting planar surfaces, including anterior surface 22a, distal surface 22b, posterior surface 22c, anterior chamfer surface 22d, and posterior chamfer surface 22e. Accordingly, as shown in FIG. 1, the virtual resection of distal end $F_d$ of model femur F includes defining a plurality of intersecting cut planes 12a-12e including anterior cut plane 12a, distal cut plane 12b, posterior cut plane 12c, anterior chamfer cut plane 12d, and posterior chamfer cut plane 12e, which correspond to the plurality of intersecting planar surfaces 22a-22e of model prosthesis 20 (FIG. 4). As illustrated in FIGS. 2 and 3, cut planes 12a-12e intersect one another at femoral cut plane vertices 14a-14d. More particularly, anterior cut plane 12a intersects anterior chamfer cut plane 12d at vertex 14a. Anterior chamfer cut plane 12d intersects distal cut plane 12b at vertex 14b, Distal cut plane 12b intersects posterior chamfer cut plane 12e at vertex 14c. Posterior chamfer cut plane 12e intersects posterior cut plane 12c at vertex 14d.

Referring still to FIGS. 1 and 2, femoral profile 16, shown as a dotted line, of the virtually resected model femur F is prepared by outlining cut planes 12a-12e extending between cut plane vertices 14a-14d. Two-dimensional outline or footprint 18 of the resected surface of model femur F is then obtained, as shown in FIG. 3, by unfolding or bending profile 16 at cut plane vertices 14a-14d until cut planes 12a-12e are aligned in a single plane. The suitable software mentioned above may be used to manipulate profile 16 to create two-dimensional outline 18.

Figure 5:
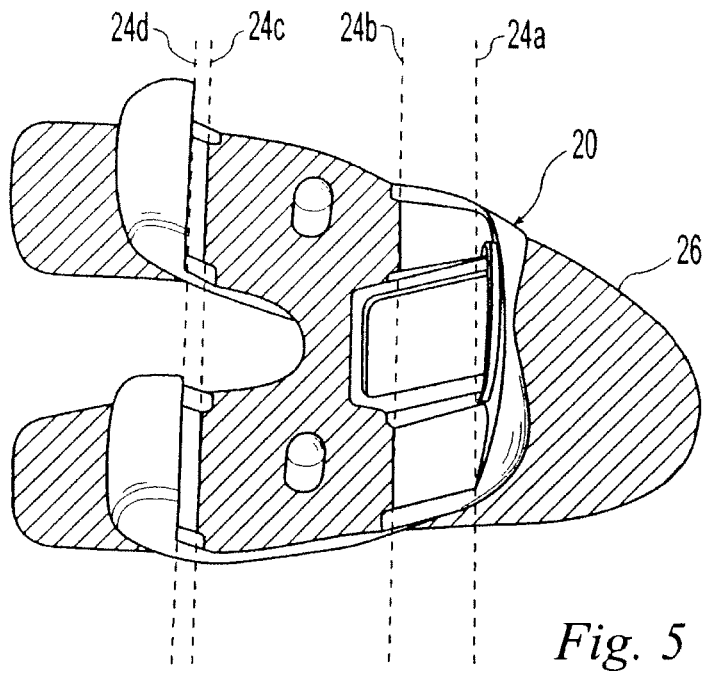
FIG. 5 is a perspective view of the prosthesis of FIG. 4, further illustrating the step of virtually unfolding the prosthesis.
Figure 6:
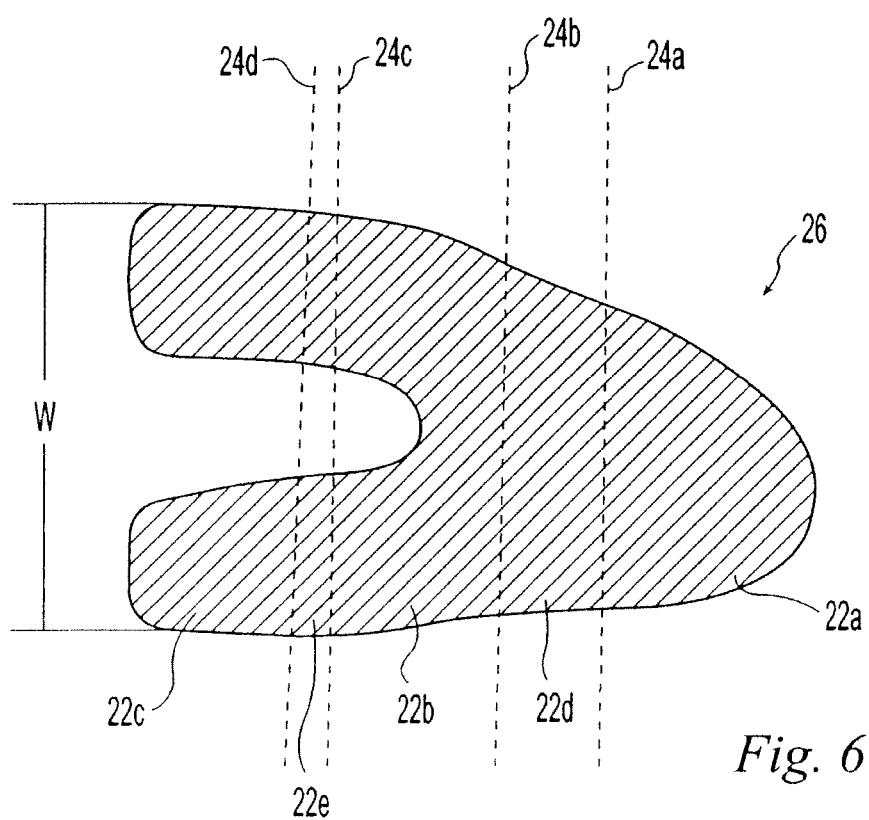
FIG. 6 is a top view of the two-dimensional outline of the prosthesis of FIG. 4 after the unfolding step of FIG. 5.

Referring now to FIGS. 4-6, two-dimensional outline or footprint 26 of proposed prosthesis 20 may be made using a process similar to that described above for outline or footprint 18 of femoral profile 16. More particularly, 3-D digital model 20 of a femoral prosthesis may be obtained using any known method and any suitable software, including those described above. As discussed above, model prosthesis 20 includes bone engaging surface 22, which includes anterior planar surface 22a, distal planar surface 22b, posterior planar surface 22c, anterior chamfer planar surface 22d, and posterior chamfer planar surface 22e. Planar surfaces 22a-22e intersect one another at prosthesis vertices 24a-24d. More particularly, anterior planar surface 22a intersects anterior chamfer surface 22d at vertex 24a, Anterior chamfer surface 22d intersects distal planar surface 22b at vertex 24b. Distal planar surface 22b intersects posterior chamfer surface 22e at vertex 24c, and posterior chamfer surface 22e intersects posterior surface 22c at vertex 24d, Anterior planar surface 22a of prosthesis 20 corresponds to anterior cut plane 12a of femur F; anterior chamfer surface 22d of prosthesis 20 corresponds to anterior chamfer cut plane 12d of femur F; distal planar surface 22b of prosthesis 20 corresponds to distal cut plane 12b of femur F; posterior chamfer surface 22e of prosthesis 20 corresponds to posterior chamfer cut plane 12e of femur F; posterior surface 22c of prosthesis 20 corresponds to posterior cut plane 12c of femur F; vertex 24a of prosthesis 20 corresponds to vertex 14a of femur F; vertex 24b of prosthesis 20 corresponds to vertex 14b of femur F; vertex 24c of prosthesis 20 corresponds to vertex 14c of femur F; and vertex 24d of prosthesis 20 corresponds to vertex 14d of femur F.

Referring to FIG. 4, prosthesis (profile 25 of model prosthesis 20 is prepared by outlining the perimeter of intersecting planar surfaces 22a-22e between prosthesis vertices 24a-24d. Prosthesis profile 25 is represented by the heavy dashed line extending about the perimeter of model prosthesis 20. Turning to FIGS. 5 and 6, two-dimensional outline or footprint 26 of prosthesis profile 25 is created by using the suitable software to unfold or bend profile 25 at vertices 24a-24d until planar surfaces 22a-22e are aligned within a single plane.

Prosthesis outline 26 may be visually compared with femur outline 18 to determine and assess whether model prosthesis 20 is a suitable fit for model femur 10, Thus, a surgeon may compare outline 26 with outline 18 and determine whether prosthesis 20 corresponding to outline 26 is an acceptable prosthesis to use for femur F. Prosthesis outline 26 may be compared with femur outline 18 by superimposing one atop the other and observing the overlapping shapes and the differences therebetween. Furthermore, using the suitable software mentioned above, quantitative analysis may be made of outlines 26 and 18. For instance, measurements of outlines 26 and 18 may be taken and the suitable software can calculate deviations between the measurements, For example, width measurements of outlines 26 and 18 at the intersections of each planar surface may be taken and/or at midpoints of each planar surface between such intersections with other planar surfaces. Any deviations between outlines 26 and 18 may then be used to calculate proposed changes in prosthesis 20 to thereby reshape prosthesis 20 to minimize the deviations. Alternatively, any deviations between outlines 26 and 18 may prompt a user to select a different prosthesis 20 and perform die same analysis to assess the fit of the second prosthesis 20 on model femur 10, i.e., if a surgeon decides that outline 26 of a first prosthesis 20 is unacceptable for femur F, then the surgeon then compares the outline 26 of another prosthesis 20 until an acceptable prosthesis is identified.

The method described above has several useful, practical applications. For example, the method described above may be used to develop new and improved existing prosthesis designs. It is contemplated that this method may be used to survey a large population of subjects to develop statistics and identify trends in bone shapes, and to adapt prosthesis sizes and shapes accordingly. More specifically, two-dimensional footprints of virtually resected bones of a large population of patients may be obtained and compared to two-dimensional footprints of numerous available prostheses.

Figure 7:
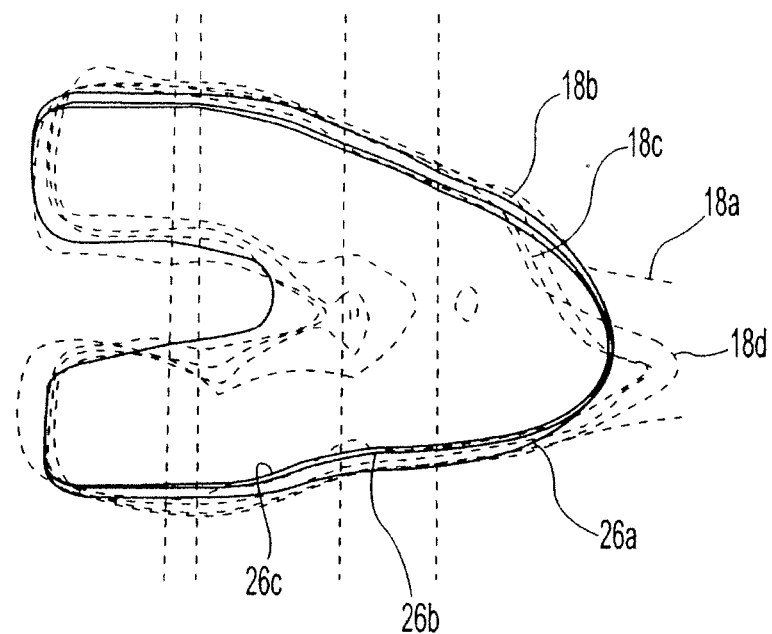
FIG. 7 is an illustration of another step of the method of the present disclosure wherein outlines of several exemplary prostheses are compared with outlines of several virtually resected exemplary femurs.
Figure 8:
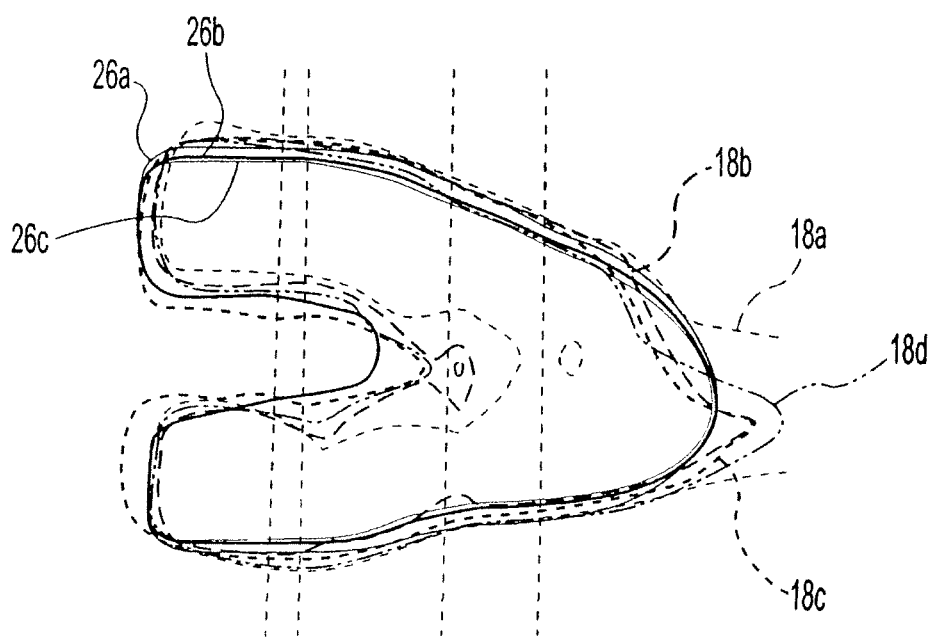
FIG. 8 is another illustration of the step shown in FIG. 7.

FIGS. 7 and 8 illustrate an exemplary application of the methods of the present disclosure. FIG. 7 illustrates femur footprints or outlines 18a-18d, shown as dotted lines, taken from a virtually resected model of a femur of four different subjects compared with footprints Or outlines 26a-26c, shown in solid lines, taken from three different models of available prostheses. FIG. 8 illustrates the same footprints 18a-18d, 26a-26c. The comparison shown in FIGS. 7 and 8 demonstrates that the prosthesis yielding footprint 26a is larger in width W (FIG. 6) than the virtually resected bones yielding footprints 18b-18d. In an exemplary embodiment, outlines 18a-18d may be used to design or create a prosthesis which substantially matches at least some of outlines 18a-18d. For example, a prosthesis may be created or designed which is a best fit approximation to a plurality of outlines 18 which may be based on a specific patient population, such as the female population.

In an exemplary embodiment, a method of the present disclosure may be performed on the femurs of a large population of women to obtain medial/lateral and anterior/posterior dimensions of the femurs and calculate ratios between the medial/lateral and anterior/posterior dimensions. These dimensions and calculations may be used in designing femoral components for use on female anatomy. In another exemplary embodiment, a method of the present disclosure may also be used to obtain medial/lateral and anterior/posterior dimensions of existing femoral components and calculate ratios between the medial/lateral and anterior/posterior dimensions of the femoral components. The dimensions and calculated ratios may then be used to compare existing femoral components to the dimensions and calculated ratios of the femurs of women to identify areas of the femoral component where fit can be optimized. Such a comparison is fully described in U.S. patent application Ser. No. 11/611,021, entitled DISTAL FEMORAL, KNEE PROSTHESES, assigned to the assignee of the present application, the disclosure of which is hereby expressly incorporated herein by reference. The same type of process may be performed for other populations, such as a population of males, various ethnic populations, populations based on age, stature-based populations, and/or populations based on disease progression or disease status.

In addition, the method described above may be used in guiding the design and manufacture of custom prostheses. For instance, a patient's femur may be modeled, virtually resected and footprinted as described above. The footprint could then be used as the footprint for forming a prosthesis.

Although the method described above is exemplified with reference to the distal end of the femur and femoral prostheses, the methods of the present invention may be applied to any bone and any prosthesis.

While this invention has been described as having exemplary designs, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

What is claimed is:

1. A method of designing a prosthesis to substantially fit a resected bone surface based on a population of bones from a plurality of patients, the method comprising the steps of:
    creating a plurality of two-dimensional outlines corresponding to each resected bone surface for each bone of the population of bones from the plurality of patients using a computer, wherein the creating step comprises:
        obtaining a three-dimensional contour of each resected bone surface based upon images of the population of bones;
        identifying a vertex between a first planar surface of each resected bone surface and a second planar surface of each resected bone surface;
        manipulating the first planar surface to be coplanar with the second planar surface; and
        outlining a perimeter of the first planar surface and the second planar surface to define the two-dimensional outline for each resected bone surface;
    determining a contour of a bone engaging surface of a prosthesis using the plurality of two-dimensional outlines and a best fit approximation of the plurality of two-dimensional outlines of the resected bone surface; and
    comparing the contour to the plurality of two-dimensional outlines of the resected bone surface derived from the population of bones from the plurality of patients to assess a fit of the prosthesis with the population of bones.

2. The method of claim 1, wherein manipulating the first planar surface to be coplanar with the second planar surface includes unfolding a three-dimensional outline.

3. A method of creating a prosthesis for placement on a resected bone surface of a bone, the method comprising the steps of:
 creating a two-dimensional outline of the resected bone surface using a computer, wherein the creating step comprises:
  obtaining a three-dimensional contour of the resected bone surface based upon an image of the bone,
  identifying a vertex between a first planar surface of the resected bone surface and a second planar surface of the resected bone surface,
  manipulating the first planar surface to be coplanar with the second planar surface,
  outlining a perimeter of the first planar surface and the second planar surface to define the two-dimensional outline of the resected bone surface; and
 determining a contour of a bone engaging surface of a prosthesis using the two-dimensional outline of the resected bone surface, wherein the determining step comprises:
  measuring the two-dimensional outline of the resected bone surface and a two-dimensional outline of the prosthesis, and
  determining a deviation between the two-dimensional outline of the resected bone surface and the two-dimensional outline of the prosthesis based on the measuring step; and
 comparing the two-dimensional outline of the resected bone surface with the two-dimensional outline of the prosthesis to assess a fit of the prosthesis with the bone.

4. The method of claim 3, wherein the resected bone surface is defined by a plurality of intersecting cut planes, wherein the step of creating the two-dimensional outline of the resected bone surface includes the step of outlining the plurality of intersecting cut planes to obtain a three-dimensional profile of the resected bone surface, the two-dimensional outline of the resected bone surface being based on the three-dimensional profile of the resected bone surface.

5. The method of claim 3, wherein the step of determining a contour of a bone engaging surface of a prosthesis using the two-dimensional outline of the resected bone surface includes the step of manipulating a three-dimensional profile of the resected bone surface to form the two-dimensional outline of the resected surface.

6. The method of claim 3, wherein the prosthesis includes at least one surface configured to be positioned adjacent to the resected bone surface, and wherein a two-dimensional outline of the prosthesis corresponds to the at least one surface of the prosthesis.

7. The method of claim 3, wherein manipulating the first planar surface to be coplanar with the second planar surface includes unfolding a three-dimensional outline.

8. A method of creating a prosthesis for placement on a resected bone surface of a bone, the method comprising the steps of:
 obtaining a three-dimensional model of the bone based upon an image of the bone;
 virtually resecting the three-dimensional model of the bone using a computer by defining a plurality of cut planes based upon a proposed prosthesis design and known surgical techniques specified for the proposed prosthesis design;
 preparing a bone profile of the virtual resection of the bone;
 creating a two-dimensional outline of the resected bone surface including manipulating a first planar surface to be coplanar with a second planar surface;
 creating a two-dimensional outline from a profile of a prosthesis based on a three-dimensional contour of a surface of the prosthesis; and
 comparing the two-dimensional outline of the resected bone surface with the two-dimensional outline of the profile of the prosthesis to assess a fit of the prosthesis with the bone.

9. The method of claim 8, wherein the two-dimensional outline of the resected bone surface includes a two-dimensional outline of the first planar surface coplanar with the second planar surface.

10. The method of claim 8, wherein the comparing the two-dimensional outline of the resected bone surface with the two-dimensional outline of the profile of the prosthesis comprises the steps of measuring the two-dimensional outline of the resected bone surface and the two-dimensional outline of the profile of the prosthesis and determining a deviation between the two-dimensional outline of the resected bone surface and the two-dimensional outline of the profile of the prosthesis based on the measuring step.

11. The method of claim 8, wherein manipulating the first planar surface to be coplanar with the second planar surface includes unfolding a three-dimensional outline.

\* \* \* \* \*